US00PP30931P2

(12) United States Plant Patent
Steffen

(10) Patent No.: US PP30,931 P2
(45) Date of Patent: Oct. 8, 2019

(54) ***ANGELONIA* PLANT NAMED 'ANCASWHI'**

(50) Latin Name: *Angelonia angustifolia*
Varietal Denomination: Ancaswhi

(71) Applicant: Elke Steffen, Erfurt (DE)

(72) Inventor: Elke Steffen, Erfurt (DE)

(73) Assignee: Elsner pac Jungpflanzen GbR, Dresden (DE)

( * ) Notice: Subject to any disclaimer, the term of this patent is extended or adjusted under 35 U.S.C. 154(b) by 0 days.

(21) Appl. No.: 15/999,968

(22) Filed: Sep. 4, 2018

(51) Int. Cl.

| | |
|---|---|
| ***A01H 5/02*** | (2018.01) |
| ***A01H 6/68*** | (2018.01) |
| ***A01H 5/00*** | (2018.01) |

(52) U.S. Cl.
USPC ..... Plt./404
CPC ..... *A01H 6/68* (2018.05); *A01H 5/00* (2013.01); *A01H 5/02* (2013.01)

(58) Field of Classification Search
USPC ..... Plt./404
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Angelonia* plant named 'Ancaswhi' characterized by its upright to trailing plant habit; moderately vigorous growth habit; freely branching habit; early and freely flowering habit; large white-colored flowers; and good garden performance.

2 Drawing Sheets

Botanical designation: *Angelonia angustifolia.*
Cultivar denomination: 'ANCASWHI'.

BACKGROUND OF THE INVENTION

The present invention relates to a new and distinct cultivar of *Angelonia* plant, botanically known as *Angelonia angustifolia* and hereinafter referred to by the name 'Ancaswhi'.

The new *Angelonia* plant is a product of a planned breeding program conducted by the Inventor in Dresden, Germany. The objective of the breeding program is to create new freely-flowering *Angelonia* plants with attractive flower coloration and long flowering period.

The new *Angelonia* plant originated from a cross-pollination made by the Inventor during the summer of 2014 in Dresden, Germany of two unnamed proprietary selections of *Angelonia angustifolia*, not patented. The new *Angelonia* plant was discovered and selected by the Inventor as a single flowering plant within the progeny of the stated cross-pollination in a controlled greenhouse environment in Dresden, Germany during the summer of 2015.

Asexual reproduction of the new *Angelonia* plant by terminal cuttings in a controlled greenhouse environment in Dresden, Germany since the summer of 2015 has shown that the unique features of this new *Angelonia* plant are stable and reproduced true to type in successive generations.

SUMMARY OF THE INVENTION

Plants of the new *Angelonia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Ancaswhi'. These characteristics in combination distinguish 'Ancaswhi' as a new and distinct *Angelonia* plant:

1. Upright to trailing plant habit.
2. Moderately vigorous growth habit.
3. Freely branching habit.
4. Early and freely flowering habit.
5. Large white-colored flowers.
6. Good garden performance.

Plants of the new *Angelonia* differ from plants of the parent selections primarily in plant and flowering habit as plants of the new *Angelonia* are more freely branching and freely flowering than plants of the parent selections.

Plants of the new *Angelonia* can be compared to plants of *Angelonia hybrida* 'Lotrawhi', disclosed in U.S. Plant Pat. No. 26,235. In side-by-side comparisons, plants of the new *Angelonia* and 'Lotrawhi' differ primarily in the following characteristics:

1. Plants of the new *Angelonia* are taller and more upright than plants of 'Lotrawhi'.
2. Plants of the new *Angelonia* are more vigorous than plants of 'Lotrawhi'.
3. Plants of the new *Angelonia* have larger flowers than plants of 'Lotrawhi'.

BRIEF DESCRIPTION OF THE PHOTOGRAPHS

The accompanying colored photographs illustrate the overall appearance of the new *Angelonia* plant showing the colors as true as it is reasonably possible to obtain in colored reproductions of this type. Colors in the photographs may differ slightly from the color values cited in the detailed botanical description which accurately describe the colors of the new *Angelonia* plant.

The photograph on the first sheet comprises a side perspective view of a typical flowering plant of 'Ancaswhi' grown in a container.

The photograph on the second sheet is a close-up view of a typical flowering plant of 'Ancaswhi'.

DETAILED BOTANICAL DESCRIPTION

Plants used for the aforementioned photograph and the following observations, measurements and values were grown during the summer and autumn in 19-cm containers in a glass-covered greenhouse in Dresden, Germany and under cultural practices typical of commercial *Angelonia* production. During the production of the plants, day temperatures were at a minimum of 20° C., night temperatures were at a minimum of 16° C. and light levels ranged from 15 kilolux to 100 kilolux. Plants were pinched two times, two and six weeks after planting rooted young plants. Plants were six months old when the description was taken and seven months old when the photograph was taken. In the following description, color references are made to The Royal Horticultural Society Colour Chart, 1995 Edition, except where general terms of ordinary dictionary significance are used.

Botanical classification: *Angelonia angustifolia* 'Ancaswhi'.

Parentage:

*Female, or seed, parent*.—Unnamed proprietary selection of *Angelonia angustifolia*, not patented.

*Male, or pollen, parent*.—Unnamed proprietary selection of *Angelonia angustifolia*, not patented.

Propagation:

*Type*.—By terminal cuttings.

*Time to initiate roots, summer and winter*.—About 20 days at temperatures about 20° C.

*Time to produce a rooted young plant, summer and winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; moderately dense.

Plant description:

*Plant form and growth habit*.—Herbaceous perennial; upright to trailing plant habit; freely branching habit; when pinched, about ten to twelve lateral branches develop per plant; moderately vigorous growth habit; moderate growth rate.

*Plant height*.—About 25 cm to 30 cm.

*Plant width* (*spread*).—About 40 cm.

*Lateral branches*.—Length: About 25 cm to 30 cm. Diameter: About 2 mm to 3 mm. Internode length: About 1 cm to 2 cm. Strength: Moderately strong. Texture: Slightly pubescent. Color: Close to 144A.

Leaf description:

*Arrangement*.—Opposite, decussate; simple; sessile.

*Length*.—About 2 cm to 8 cm.

*Width*.—About 8 mm to 12 mm.

*Shape*.—Lanceolate to oblong.

*Apex*.—Acute.

*Base*.—Attenuate.

*Margin*.—Serrate.

*Texture and luster, upper and lower surfaces*.—Smooth, glabrous; leathery; glossy.

*Venation pattern*.—Pinnate.

*Color*.—Developing leaves, upper surface: Close to 137B. Developing leaves, lower surface: Close to 137D. Fully expanded leaves, upper surface: Close to 137A; venation, close to 137A. Fully expanded leaves, lower surface: Close to 137C; venation, close to 145B.

Flower description:

*Flower type and flowering habit*.—Single flowers arranged in upright to outward terminal racemes; flowers face mostly outwardly; freely flowering habit; full dense inflorescences.

*Fragrance*.—None detected.

*Natural flowering season*.—Plants begin flowering about nine to ten weeks after planting rooted young plants; in the garden, flowering is continuous from mid-May until frost in Central Europe.

*Postproduction longevity*.—Flowers last about 20 days on the plant; flowers not persistent.

*Flower buds*.—Height: About 5 mm. Diameter: About 5 mm. Shape: Globose. Color: Close to 145B.

*Inflorescence length*.—Inflorescences are indeterminate and continue to grow longer during the flowering season.

*Inflorescence diameter*.—About 6 cm to 7 cm.

*Flower diameter*.—About 2.8 cm by 3 cm.

*Flower length*.—About 1 cm.

*Petals*.—Quantity per flower: Typically five in a single whorl; petals fused at the base into a tubular throat. Length: About 1 cm to 1.4 cm. Width: About 1.2 cm to 1.5 cm. Shape: Roughly spatulate. Apex: Rounded. Margin: Entire, undulate. Texture, upper and lower surfaces: Smooth, glabrous; velvety. Color: When opening, upper and lower surfaces: Close to 145C. Fully opened, upper and lower surfaces: Close to 155D; color does not change with development. Throat: Close to 145C and 155D. Tube: Close to 155D.

*Sepals*.—Quantity per flower: Typically five in a single whorl. Length: About 4 mm. Width: About 2 mm. Shape: Ovate. Apex: Acute. Margin: Entire. Texture, upper and lower surfaces: Smooth, glabrous. Color, upper surface: Close to 137A. Color, lower surface: Close to 137B.

*Pedicels*.—Length: About 1 cm to 2 cm. Diameter: About 1 mm. Angle: Outward to slightly upright, less than 90° from vertical. Strength: Moderately strong; flexible. Texture: Slightly pubescent. Color: Close to 146C.

*Reproductive organs*.—Stamens: Quantity per flower: Typically four. Filament length: About 3 mm. Filament color: Close to 155D. Anther length: About 2 mm. Anther shape: Elliptic. Anther color: Close to 90A. Pollen amount: Moderate. Pollen color: Close to 155D. Pistils: Quantity per flower: One. Pistil length: About 3 mm. Stigma shape: Tapering. Stigma color: Close to 155D. Style length: About 3 mm. Style color: Close to 155D. Ovary color: Close to 142B.

*Fruits*.—Length: About 4 mm. Diameter: About 4 mm. Color: Close to 165D.

*Seeds*.—Quantity per flower: About 30 to 50. Length: Less than 1 mm. Diameter: Less than 1 mm. Color: Light brown.

Disease & pest resistance: To date, plants of the new *Angelonia* have not been noted to be resistant to pathogens and pests common to *Angelonia* plants.

Garden performance: Plants of the new *Angelonia* have been observed to have good garden performance and tolerate rain, wind and temperatures ranging from about 1° C. to 30° C.

It is claimed:

1. A new and distinct *Angelonia* plant named 'Ancaswhi' as illustrated and described.

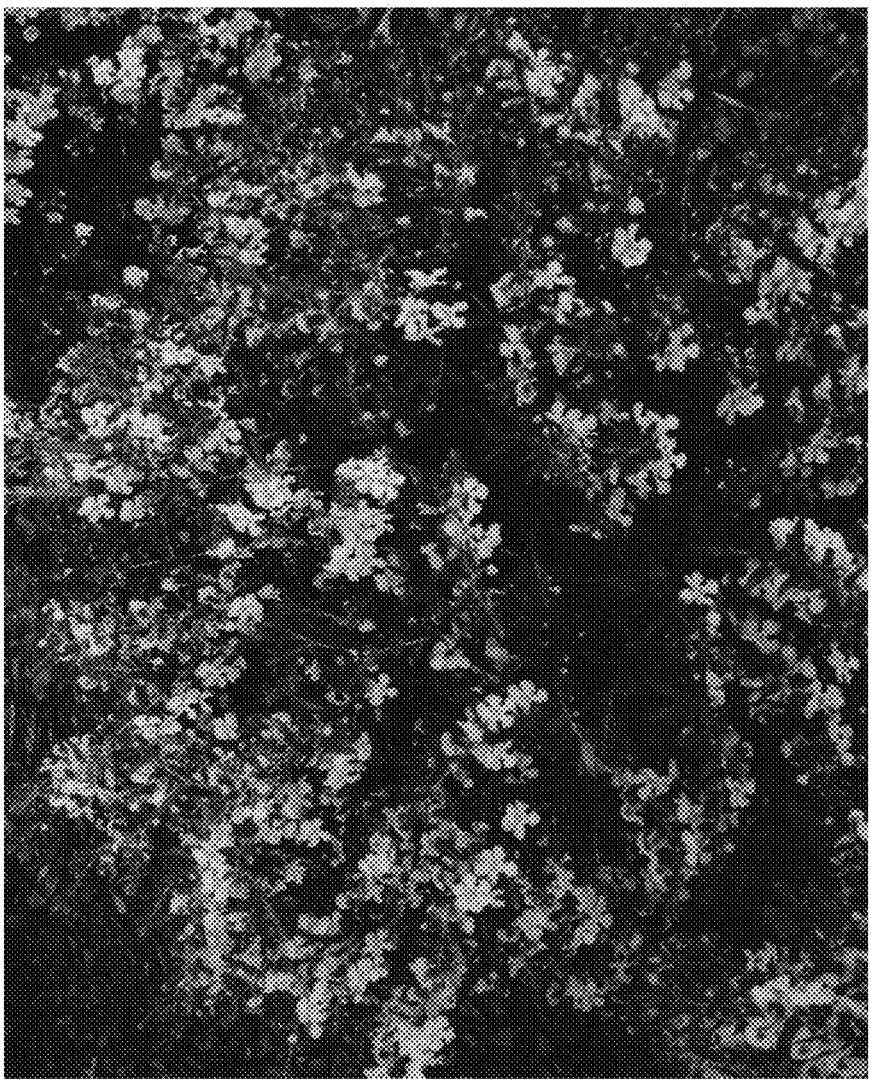

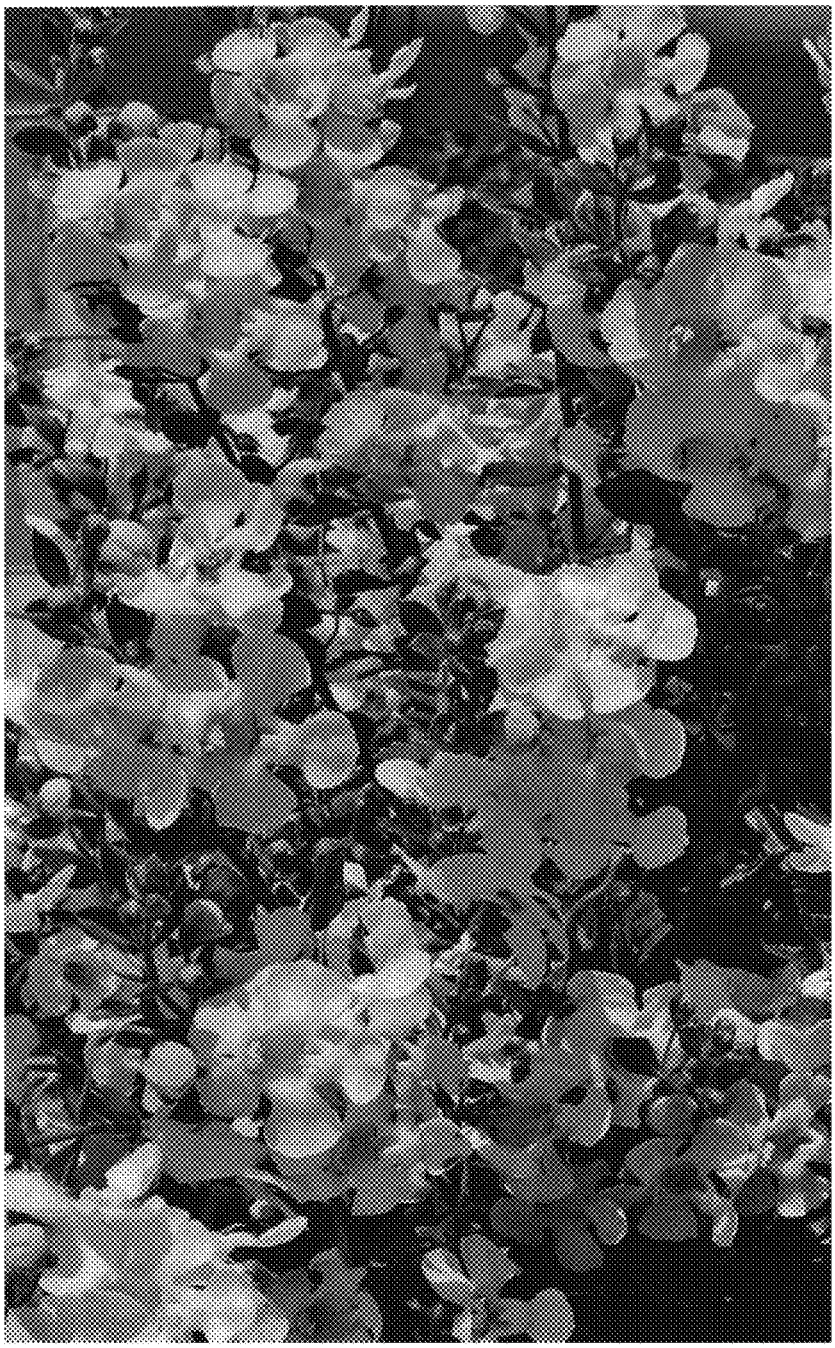

* * * * *